United States Patent
Heinz et al.

(10) Patent No.: US 6,296,893 B2
(45) Date of Patent: Oct. 2, 2001

(54) PHARMACEUTICAL PACKING DEVICE COMPRISING A HOLLOW PLASTIC BODY HAVING AN IMPROVED INTERNAL LUBRICANT LAYER AND METHOD OF MAKING SAME

(75) Inventors: Jochen Heinz, Vendersheim; Michael Spallek, Ingelheim; Gerhard Weber, Bechenheim, all of (DE)

(73) Assignee: Schott Glass, Mainz (DE)

(*) Notice: Subject to any disclaimer, the term of this patent is extended or adjusted under 35 U.S.C. 154(b) by 0 days.

(21) Appl. No.: 09/205,165

(22) Filed: Dec. 4, 1998

(30) Foreign Application Priority Data

Dec. 4, 1997 (DE) .............................. 197 53 766

(51) Int. Cl.$^7$ .............................. B05D 3/00; B05D 7/22; A61F 13/20
(52) U.S. Cl. .................. 427/2.28; 427/230; 427/236; 427/489; 427/515; 427/256
(58) Field of Search .................. 427/2.28, 230, 427/236, 487, 489, 515, 256; 604/15

(56) References Cited

U.S. PATENT DOCUMENTS

| | | |
|---|---|---|
| 4,509,981 | 4/1985 | Sanders, Jr. et al. . |
| 4,720,521 * | 1/1988 | Spielvogel et al. ............... 524/862 |
| 4,767,414 * | 8/1988 | Williams et al. ................ 604/230 |
| 4,806,430 | 2/1989 | Spielvogel et al. . |
| 4,844,986 | 7/1989 | Karakelle et al. . |
| 5,338,312 | 8/1994 | Montgomery . |
| 5,456,940 * | 10/1995 | Funderburk ..................... 427/2.1 |
| 5,587,244 * | 12/1996 | Flinchbaugh ................... 428/447 |
| 5,603,991 * | 2/1997 | Kupiecki et al. ................ 427/508 |
| 5,788,670 * | 8/1998 | Reinhard et al. ................ 604/89 |
| 6,008,298 * | 12/1999 | Hatke et al. .................... 525/210 |
| 6,145,277 * | 11/2000 | Lawecki et al. ................ 53/428 |
| 6,170,940 * | 1/2001 | Shinada et al. ................. 347/86 |
| 6,189,292 * | 2/2001 | Odell et al. .................... 53/425 |
| 6,191,203 * | 2/2001 | Asrar et al. .................... 524/317 |

FOREIGN PATENT DOCUMENTS

| | | |
|---|---|---|
| 196 52 708 A1 | 6/1998 | (DE) . |
| 0 227 340 A2 | 7/1987 | (EP) . |
| 0 201 915 B1 | 1/1990 | (EP) . |
| 0 329 041 B1 | 5/1993 | (EP) . |
| 0 302 625 B1 | 10/1993 | (EP) . |
| 0 709 105 A1 | 5/1996 | (EP) . |
| 0 756 901 A1 | 2/1997 | (EP) . |

* cited by examiner

Primary Examiner—Shrive P. Beck
Assistant Examiner—Jennifer Kolb
(74) Attorney, Agent, or Firm—Michael J. Striker

(57) ABSTRACT

The pharmaceutical packing device has a hollow plastic body (1) of axial length (I) and a cylindrical portion (7) extending over at least a part of its axial length and an interior silicone lubricant layer (3) provided on an interior surface of the plastic body in the cylindrical portion (7). The lubricant layer (3) provides a sliding surface for a flexible piston (4) slidably mounted in the hollow plastic body, thus forming an injector device. The silicone lubricant layer (3) is made by a method including preparing a mixture of reactive silicone oil and non-reactive silicone oil, applying this mixture to the interior surface at a temperature of at least 40° C. in a single step without activation of the surface to form a preliminary layer and cross-linking the reactive silicone oil in the preliminary layer to form the silicone lubricant layer.

4 Claims, 1 Drawing Sheet

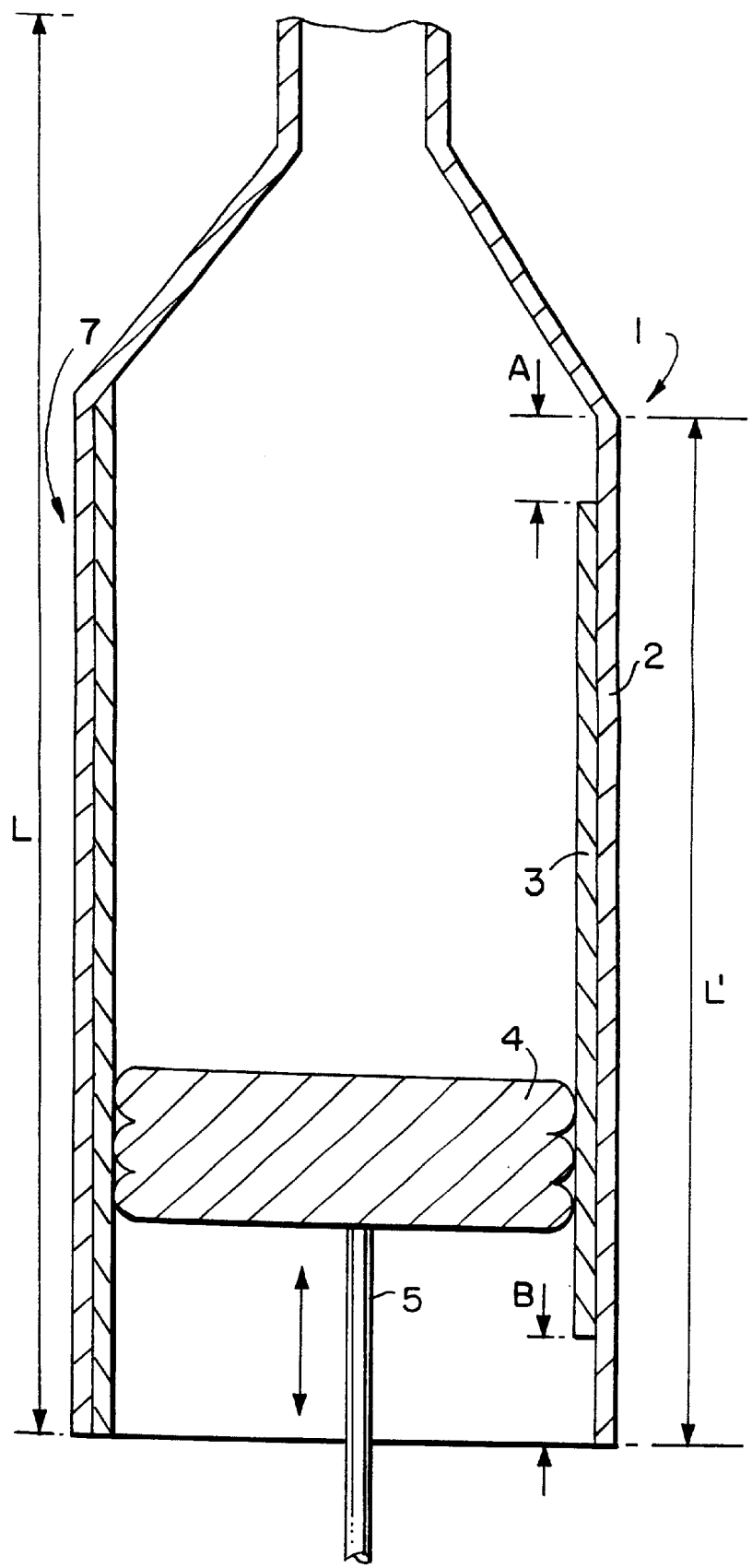

PHARMACEUTICAL PACKING DEVICE COMPRISING A HOLLOW PLASTIC BODY HAVING AN IMPROVED INTERNAL LUBRICANT LAYER AND METHOD OF MAKING SAME

BACKGROUND OF THE INVENTION

1. Field of the Invention

The invention relates to a pharmaceutical packing or filling device, which comprises an extended or elongated hollow plastic body having an axial length and a cylindrical portion extending over at least part of the axial length, which is provided with an interior silicone lubricant layer in this cylindrical portion and which is tightly closed by a stopper. It also relates to a method of making this pharmaceutical packing or filling device.

2. Prior Art

In the pharmaceutical packing device comprising the extended hollow plastic body an elastomeric closing member, e.g. a piston or a piston stopper, is inserted in its hollow interior space, and is slidable in the extended hollow plastic body, bearing flexibly on its interior wall. Typical examples include plastic syringe cylinders for pre-filled syringes, injector devices for cylindrical ampoules and capsules, and also piston burettes in analytical chemistry applications.

In order to overcome various problems typically a silicone lubricant layer is provided on the interior wall of the hollow plastic body.

According to U.S. Pat. No. 4,767,414 and European Patent EP 0 201 915 B1 silicone oil is applied to the surface of the interior wall. In the method described in these references the surface is activated with ionizing plasma to obtain good adherence and the silicone oil applied to it is similarly treated with ionizing plasma.

This process is comparatively inconvenient. Also the silicone oil is comparatively non-reactive, i.e. free silicone oil, which is exposed to the contents of the hollow plastic body in operation of the piston. The introduction of the silicone oil in the human body in the case of injectors should be reduced to a minimum for known reasons. U.S. Pat. No. 4,844,986 describes a process for providing a silicone lubricant layer to the interior wall of the hollow plastic body by means of plasma polymerization for preparation of a coating of polydimethylsiloxane.

Also this process requires activation of the plastic surface and a multistep application process.

European Patent Document EP 0 329 041 describes a process for coating the interior wall of a hollow plastic body with a polysiloxane, or polysilane or polysilazane by means of an ionizing plasma, whereby an adherent layer of this material is first produced and then a thin lubricant layer is applied over it.

Also this process requires activation of the plastic surface and comprises many steps.

The same is true of the process described in EP 0 302 625 B1, according to which the surface of the interior wall of the hollow plastic body is first treated with plasma in order to obtain a plasma treated polymer surface. Then a layer of a polysiloxane lubricant is applied to that surface without plasma treatment. The polysiloxane lubricant is provided with a suitable predetermined surface tension so that it will wet the plasma treated surface completely.

Finally U.S. Pat. No. 5,338,312 describes a coating for the interior wall of a hollow plastic body, on which two lubricant layers are applied over each other, namely a base layer of silicone oil with a higher viscosity applied on the interior wall by means of an adhesive layer and a surface layer of silicone oil with a lower viscosity. The silicone oils of the individual layers are preferably cross-linked by means of ionized plasma.

Similarly expensive process engineering is required to provide the lubricant layers in this last process. Among other things, the surface layer contains much free, i.e. non-reactive, silicone oil.

SUMMARY OF THE INVENTION

It is an object of the present invention to provide a pharmaceutical packing device of the above-described type comprising an extended or elongated hollow plastic body having a cylindrical portion extending over at least part of its axial length, which is provided with a silicone lubricant layer in this cylindrical portion and which is tightly closed by a stopper, which is structured so that it can be made in a simple manner by a single stage process and so that the contamination of the contents of hollow plastic body with silicone droplets is minimized.

It is also an object of the invention to provide a method of making the pharmaceutical packing device of the above-described type that is simple, that consists of a single stage process without contamination of the contents of the container with silicone droplets.

According to the invention the lubricant layer is made from a mixture of reactive silicone oil with non-reactive silicone oil.

The process for making the pharmaceutical packing device comprising the hollow plastic body that attains the above-described objects comprises the following steps:

a) forming the hollow plastic body with known engineering methods;

b) preparing a mixture of reactive silicone oil with non-reactive silicone oil;

c) applying the mixture of the silicone oils to the interior wall of the hollow plastic body on the cylindrical portion of the hollow plastic body to form a preliminary or precursor layer with known methods;

d) cross-linking the mixed silicone oils in the preliminary layer to form the lubricant layer; and e) processing the hollow plastic body provided with the lubricant layer according to its predetermined application. The principle feature of the invention thus is the use of a mixture of reactive silicone oil and non-reactive silicone oil. It is especially surprising that use of this type of mixture does not require activation of the surface of the hollow plastic body.

According to a preferred embodiment of the invention this occurs when the plastic material, from which the hollow plastic body is made, is a cycloolefin polymer or a copolymer (COC) and the mixture of silicone oils is applied immediately after the molding or forming of the hollow plastic body to its interior wall, while the hollow plastic body is still heated, preferably at a temperature over 40° C.

The invention permits the application of the silicone lubricant layer to the hollow plastic body in a single step process, which means without expensive activation of the surface or multistep application processes. The reactive silicone oil component forms an adherent base layer after the cross-linking, in which the partially non-reactive silicone oil component is locally embedded which provides the lubrication properties.

Reactive silicone oils contain reactive functional groups, which permit cross-linking to themselves and as needed with other surfaces, in contrast to non-reactive silicone oils.

Thus a separating and lubricating layer is formed between the container (hollow plastic body) and moving elastomeric component (stopper).

The structure of the layer is based on a siloxane molecule that contains functional groups according to its hardening mechanism according to its function.

Reactive silicone oil especially contain vinyl groups, which cross-link under the influence of heat (temperature) and ultraviolet radiation (UV). Particularly the cross-linking reaction is catalyzed by platinum compounds.

The hardened silicone oil then forms a solid film, which functions as a separating layer between the hollow plastic body and the piston-like stopper. Because of that a baking of the stopper, especially when it is made of bromobutyl, onto the COC surface of the hollow plastic body is prevented. Dimethylpolysiloxane may be admixed to the reactive silicone oil as a non-reactive silicone oil for reduction of the sliding friction.

A siliconizing agent based on a reactive silicone oil is preferably formed from vinyl-group-containing silicone oil, cross-linking agent, catalyst, solvent and non-reactive dimethylpolysiloxane having a viscosity of from 350 to 20000 cSt.

The use of a mixture of reactive and non-reactive silicone oil as lubricant is already known from U.S. Pat. Nos. 4,806,430 and 4,720,521. In the known case however only metal substrates, such as injector needles, razor blades or the like, were coated. The present invention in contrast comprises an improved pharmaceutical packing device provided with the above-described coating on its plastic surfaces. There is no suggestion in the prior art that the lubricant layer on the pharmaceutical container should be provided by the above-described method according to the invention. This type of coating has not previously been used in the field of coatings for plastic bodies.

Since the substrate of the invention is entirely different, the appropriate coating process is also expected to be entirely different, especially because the adherence properties of the layer on plastic are very different from the adherence properties on metal. For example, it is known that in the painting of automobiles the painting of the metallic chassis cannot be performed in the same manner as the painting of a plastic bumper that is typically made from polyolefin. The plastic container according to the invention furthermore comprises a permeable plastic in which components of the siliconizing agent can diffuse or wander into the plastic body and thus would no longer provide the required lubrication. This problem is not present in the case of impermeable metallic substrates in which those same components cannot diffuse according to the above-described prior art. Also in pharmaceutical products the hollow plastic body is tightly sealed by an elastomeric stopper. Silicone can be dislodged by the required sealing force or similarly can diffuse into the stopper, so that it would not be possible to slide the stopper after a long storage interval.

Finally the silicone material of the hollow plastic body is exposed to liquid contact during the entire storage time of the filled pharmaceutical packing device (which is up to 5 years), which is not the case for the products according to the state of the prior art.

The cylindrical portion of the hollow plastic body may be provided with the silicone lubricant layer over its entire axial length.

However special advantages can be derived from a selective application of the silicone oil over a predetermined axial distance on the cylindrical portion, i.e. when certain regions are not coated. Additional functions can result from this type of axial coating, for example by the selective coating of certain interior regions of a syringe cylinder in which a rubber piston slides. By not coating the rear end of the syringe cylinder over about 1 cm of axial length, the withdrawal of the rubber piston from this rear end of the syringe cylinder can be prevented. This selective coating thus allows the formation of a piston brake without great expense.

On the other hand it is also possible to leave a region of about one cm width at the head or top end of the syringe cylinder without a lubricant layer. Thus the reverse effect can be obtained: since in this region the piston encounters a higher frictional resistance, but the piston may be moved up to the front end of syringe cylinder on the provided lubricant layer. Because of the absence of the lubricant layer in the front region of the cylinder interior, it is no longer possible to move the piston back into the cylinder. Thus a non-reusable injection device is provided by this very simple technique.

A very tough reactive one-component silicone may be worked into a low viscosity, non-reactive silicone oil in a mixture according to the invention, since the latter acts as a diluent or thinning agent.

The invention provides definite process advantages in comparison to the state of the art as well as additional functions to the resulting product. Also contamination of the contents by silicone droplets is definitely reduced, for example during filling of one-time-usage syringes, since the content of free, i.e. non-reactive, silicone in the lubricant layer is lowered to a minimum according to the invention.

Additional advantages of the hollow plastic body according to the invention include:

a) The difference between static friction and sliding friction in the hollow plastic body according to the invention is not as great as in the known hollow body. Because of that compression forces required by comparatively high static friction forces, which can lead for example to jerky dispensing of the contents of the injector body are avoided.

b) Improved adherence of the lubricant layer on the surface of the interior wall of the injector body is obtained.

c) It is possible to reduce the otherwise conventional siliconization of the rubber stopper that is slidable in the cylindrical portion of the hollow plastic body to a minimum.

It has been proven that the lubricant layer according to the invention can be sterilized by standard methods (typically by a steam treatment in an autoclave at 121° C. for 20 minutes), and few silicone particles are found in the contents as a result of that treatment. Its properties have no limiting changes either before or after irradiation of the body provided with the lubricant layer by high energy radiation (γ-radiation, electron beam, high energy light flash, etc).

BRIEF DESCRIPTION OF THE DRAWING

The objects, features and advantages of the invention will now be illustrated in more detail with the aid of the following description of the preferred embodiments, with reference to the accompanying figures in which:

The sole FIGURE is a longitudinal cross-sectional view through a hollow plastic body provided with an interior lubricant layer by the method according to the invention.

DESCRIPTION OF THE PREFERRED EMBODIMENTS

A syringe body for a pre-filled syringe device is shown in the figure as an extended hollow plastic body 1 with an interior lubricant layer 3 in preferred embodiments according to the invention. It is understood that the hollow plastic body 1 according to the invention can also be an injector body for a cylindrical ampoule, capsule or piston burette.

The interior wall 2 of the hollow plastic body 1 is provided with the lubricant layer 3 inside the hollow plastic body 1.

The elements of the hollow plastic body 1 in the figure are not drawn to scale in order to be able to show the applied silicone lubricant layer 3.

This silicone lubricant layer 3 is applied to a cylindrical portion 7 of the hollow plastic body 1 and extends over a portion of the total axial extent 1 of the hollow plastic body 1. It can extend over the entire length 1' of this cylindrical portion, as shown in the left part of the figure. However it can also extend as in the right part of the figure so as to leave end sections A and B uncoated. A piston 4 is positioned inside of the syringe cylinder, which is slidable by means of a detachable piston rod 5. The silicone lubricant layer 3 provides a smooth lubricated sliding motion for the piston 4. The lubricant free end section B acts as a piston brake, i.e. it prevents the piston 4 from being withdrawn from the syringe cylinder. The free end section A prevents the piston from being moved back into the interior of the injector body when the piston 4 is moved into a position at the top end of the injector body. Thus a reuse of the system is prevented so that the injector device is thus a one-time pre-filled injector device. The silicone lubricant layer 3 according to the invention comprises a mixture of reactive silicone oil of higher viscosity than the non-reactive silicone oil of lower viscosity.

The viscosity of the reactive silicone oil for a one-component system is from 10,000 to 100,000 centistokes, and from 200 to 5000 centistokes for a multi-component system. In contrast the viscosity of the non-reactive silicone oil is from 350 to 20,000 centistokes.

The silicone oil can be diluted prior to application, especially when it is applied by spraying.

The thickness of the silicone lubricant layer 3 is in a range of from 10 nm to 1 μm.

The proportion of free, i.e. non-reactive, silicone oil depends on the proportion of solvent and the viscosity of the reactive silicone oil being employed. It is in a range of from 5% to 85% relative to the total amount of the mixture.

The silicone oils can comprise the following silicone compounds:

Non-cross-linked polar silicones or polysiloxanes, especially non-reactive polydimethyldisiloxane (PDMS) or reactive polymeric siloxane, copolymers of alkylamine-modified methoxysiloxanes and polysiloxane with an aminoalkyl group.

The cross-linking occurs with known methods, especially with UV light or by plasma polymerization.

The plastic material, from which the hollow plastic body 1 is made, must meet special requirements for concrete applications. In applications which require good dimensional accuracy, as with injector bodies and burette cylinders for piston burettes, a comparatively rigid plastic is preferable, preferably a cycloolefin copolymer (COC), which is formed by injection molding processes. Advantageously an in-line method is used in which the hollow plastic body is formed in an assembly line, filled and closed. This type of process is described in prior art German Patent Application 196 52 708.2-35. Basically with this process it is possible to apply the mixture of silicone oils to its interior wall having a temperature over 40° C. immediately after the forming of the hollow plastic body, which provides an especially good adherence of the silicone lubricant layer, especially when the hollow plastic body 1 is made from a COC plastic material.

The disclosure in German Patent Application 197 53 766.9-43 of Dec. 4, 1997 is incorporated here by reference. This German Patent Application describes the invention described hereinabove and claimed in the claims appended hereinbelow and provides the basis for a claim of priority for the instant invention under 35 U.S.C. 119.

While the invention has been illustrated and described as embodied in a pharmaceutical packing device comprising a hollow plastic body with an improved internal lubricant layer and method of making same, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims:

1. A method of making a pharmaceutical packing device comprising an extended hollow plastic body (1) having an axial length (I) and a cylindrical portion (7) extending over at least a part of said axial length of said plastic body (1) and an interior silicone lubricant layer (3) provided in said cylindrical portion (7); wherein said hollow plastic body (1) is formed so as to be closed by means of a stopper (4); said method comprising the steps of:

a) forming the hollow plastic body by an injection molding technique, said hollow plastic body consisting of a cycloolefin copolymer;

b) preparing a mixture of reactive silicone oil and non-reactive silicone oil so that said mixture contains from 5 to 85 percent by weight of said non-reactive silicone oil;

c) applying said mixture prepared in step b) in a single application step to an interior surface in said cylindrical portion of the hollow plastic body immediately after said forming of step a) when said hollow plastic body has a temperature of at least 40° C. to form a preliminary layer, said applying being performed without activating the interior surface prior to the applying; and d) cross-linking said reactive silicone oil in the preliminary layer to form said silicone lubricant layer, said silicone lubricant layer consisting of an adherent base layer in which the non-reactive silicone oil is locally embedded.

2. The method as defined in claim 1, wherein said silicone lubricant layer has a thickness of from 10 nm to 1 μm.

3. The method as defined in claim 1, wherein said reactive silicone oil is a one-component system with a viscosity of from 10,000 to 100,000 centistokes or a multi-component system with a viscosity of from 200 to 5,000 centistokes, and said non-reactive silicone oil has a viscosity of from 350 to 20,000 centistokes.

4. The method as defined in claim 1, herein said applying said mixture to said interior surface consists of spraying said mixture onto said interior surface.

* * * * *